United States Patent [19]
Rinaldi et al.

[11] Patent Number: 5,547,659
[45] Date of Patent: *Aug. 20, 1996

[54] PHOTOPROTECTION COMPOSITIONS

[75] Inventors: Marie A. Rinaldi, Hamden; Larry R. Robinson, Oxford, both of Conn.

[73] Assignee: Richardson-Vicks Inc., Shelton, Conn.

[*] Notice: The term of this patent shall not extend beyond the expiration date of Pat. No. 5,306,485.

[21] Appl. No.: 88,396

[22] Filed: Jul. 7, 1993

Related U.S. Application Data

[63] Continuation of Ser. No. 696,902, May 7, 1991, abandoned.

[51] Int. Cl.$^6$ ............................................. A61K 7/42
[52] U.S. Cl. ................................... 424/59; 424/60
[58] Field of Search ................................... 424/59, 60

[56] References Cited

U.S. PATENT DOCUMENTS

| | | | |
|---|---|---|---|
| 3,215,724 | 11/1965 | Strobel et al. | 260/465 |
| 4,172,122 | 10/1979 | Kubik et al. | 424/59 |
| 4,522,807 | 6/1985 | Kaplan | 424/59 |
| 4,597,963 | 7/1986 | Deckner | 424/59 |
| 4,603,046 | 7/1986 | Georgalas et al. | 424/59 |
| 4,663,157 | 5/1987 | Brock | 424/59 |
| 4,671,955 | 6/1987 | Palinczar | 424/47 |
| 4,683,134 | 7/1987 | Palinczar | 424/59 |
| 4,686,099 | 8/1987 | Palinczar | 424/47 |
| 4,699,779 | 10/1987 | Palinczar | 424/59 |
| 4,710,371 | 12/1987 | Palinczar | 424/47 |
| 4,731,242 | 3/1988 | Palinczar | 424/59 |
| 4,781,914 | 11/1988 | Deckner | 424/59 |
| 4,810,489 | 3/1989 | Murray et al. | 424/59 |
| 4,810,490 | 3/1989 | Dixon et al. | 424/59 |
| 4,820,508 | 4/1989 | Wortzman | 424/59 |
| 4,917,882 | 4/1990 | Strobridge | 424/59 |
| 4,917,883 | 4/1990 | Strobridge | 424/59 |
| 4,919,934 | 4/1990 | Deckner et al. | 424/401 |
| 5,207,998 | 5/1993 | Robinson et al. | 424/59 |
| 5,306,485 | 4/1994 | Robinson et al. | 424/59 |

FOREIGN PATENT DOCUMENTS

| | | | |
|---|---|---|---|
| 85-141249/24 | 4/1985 | Australia | A61K 7/42 |
| WO90/11067 | 10/1990 | WIPO | A61K 7/42 |

OTHER PUBLICATIONS

Soap/Cosmetics/Specialities, "Hydrophobically Modified 'Carbopol' Resins", vol. 63, No. 5, p. 28, May 1987.
Cosmetics & Toiletries, "A New Waterproofing Agent for Sunscreen Prodcuts", vol. 102, No.3, p. 107, Mar. 1987.
Cosmetics & Toiletries, "Novel Cosmetic Emulsions", vol. 101, No. 11, p. 125, Nov. 1986.
B. F. Goodrich Technical Data Sheet No. 73, Carbopol$^R$ 1342 (1984).

*Primary Examiner*—Shelley A. Dodson
*Attorney, Agent, or Firm*—David K. Dabbiere; Anthony D. Sabatelli

[57] ABSTRACT

Disclosed are improved topical compositions having improved efficiency such as improved sunscreen effectiveness for protecting the skin from the harmful effects of ultraviolet irradiation, such as sunburn and sun-induced premature aging of the skin.

13 Claims, No Drawings

PHOTOPROTECTION COMPOSITIONS

This is a continuation of application Ser. No. 07/696,902, filed on May 7, 1991 now abandoned.

TECHNICAL FIELD

This invention relates to improved topical compositions having improved substantivity and improved efficiency such as improved sunscreen effectiveness for protecting the skin from the harmful effects of ultraviolet irradiation, such as sunburn and sun-induced premature aging of the skin.

BACKGROUND OF THE INVENTION

The damaging effects of sunlight on skin are well documented. Contrary to what most people believe, it is not necessary that one sunbathe to suffer the ill-effects of excessive UV exposure. In fact, significant damage can be done just by routine day-to-day activities in the sunlight. Some scientists estimate that over 70 percent of the damage the sun inflicts on the average person's skin over a lifetime is the result of simply being outdoors or even sitting by a window.

The major short term hazard of prolonged exposure to sunlight is erythema (i.e. sunburn). The 290 to 320 nanometer wavelength ultraviolet radiation range, designated as the "UVB" wavelength range, tends to be the primary cause of erythema. The 320 to 400 nanometer wavelength ultraviolet radiation range, designated as the "UVA" wavelength range, also produces erythema.

In addition to the short term hazard or erythema, there are also long term hazards associated with UV radiation exposure. One of these long term hazards is malignant changes in the skin surface. Numerous epidemiologic studies demonstrate a strong relationship between sunlight exposure and human skin cancer.

Another long term hazard of ultraviolet radiation is premature aging of the skin. This condition is characterized by wrinkling and yellowing of the skin, along with other physical changes such as cracking, telangiectasis (spider vessels), solar keratoses (growths), ecchymoses (subcutaneous hemorrhagic lesions), and loss of elasticity (sagging). The adverse effects associated with exposure to UVA and UVB wavelength radiation are more fully discussed in DeSimone, "Sunscreen and Suntan Products", *Handbook of Nonprescription Drugs*, 7th Ed., Chapter 26, pp. 499–511 (American Pharmaceutical Association, Washington, D.C.; 1982); Grove and Forbes, "A Method for Evaluating the Photoprotection Action of Sunscreen Agents Against UV-A Radiation", *International Journal of Cosmetic Science*, 3, pp. 15–24 (1982); and U.S. Pat. No. 4,387,089, DePolo, issued Jun. 7, 1983; the disclosures of all of which are incorporated herein by reference. Hence, although the immediate effects of ultraviolet radiation may be cosmetically and socially gratifying, the long-term hazards are cumulative and potentially serious. It has been estimated that eighty percent of lifetime sun exposure occurs during multiple brief exposures not intended to produce tanning. Therefore, photoprotection during these exposures to ultraviolet radiation is necessary.

The fact that these effects are taken seriously by the general public is suggested by considering the sun protection products' market. This market has grown considerably in recent years and many new products are introduced each year. What used to be looked upon as a seasonal business is no longer. Sun protection compounds are now included in a diversity of personal care products, particularly cosmetic-type products which are worn on a daily basis.

Physical sunblock agents are commercially available to protect the skin from UV radiation. These agents scatter, reflect, and absorb ultraviolet radiation. See, Sayre, R. M. et. al., "Physical Sunscreens", *J. Soc. Cosmet. Chem.*, vol. 41, no.2, pp. 103–109 (1990). Examples of physical sunblock agents include titanium dioxide and zinc oxide. However, compositions containing a high level of these agents are opaque, generally unattractive in color, and are viewed as unacceptable for usage on more than just the nose or tops of the ears.

The most common agents for sun protection are chemical sunscreens. These agents exert their effects through chemical means, i.e., they absorb ultraviolet radiation so that it cannot penetrate the skin. Sunscreens present the user with several problems. For example, they must be on the surface of the skin at the time of exposure to be effective. Sunscreens are preventative so one must anticipate being in the sun. To be most effective, sunscreens must be on the skin as a continuous uniform film. Delivering such a film to the uneven surface of the skin is very difficult.

Sunscreen-containing oil-in-water emulsions are the most popular form of photoprotection products in the U.S. market. This form is cosmetically pleasing, safe, cost effective and versatile. In general, however, oil-in-water emulsions containing oil-soluble sunscreens do not provide as good sunscreening efficiency when compared to water in-oil emulsions containing oil soluble sunscreens. Unfortunately water-in-oil emulsions, while providing good sunscreening efficiency, are at a disadvantage in terms of their cosmetic properties. It is therefore highly desirable to formulate oil-in-water photoprotection emulsions which possess superior cosmetic and substantive properties and improved sunscreening efficiency.

Without being limited by theory, it is believed that the specific oil-in-water dispersions of the present invention having a specific sunscreen component and vehicle and a surface tension of greater than about 30 dynes/cm, when measured as a 3.33% (w/w) aqueous solution of the emulsion, which possess a wax component having a required HLB between about 1 and about 8 and an oil phase with a required HLB of between about 1 and about 8 will form continuous oil films when applied to skin and thereby provide improved benefits such as improved substantivity as well as increased SPF efficiency. The compositions of the present invention further provide reduced sunscreen migration thereby reducing, for example, eye-stinging, by inhibiting the sunscreen active from invading the eye area.

It is therefore an object of the present invention to provide a topical composition in a stable form, the use of which will prevent both acute (erythema) and chronic (photoaging) effects of exposure to the sun.

It is further an object of the present invention to provide specific photoprotection emulsion compositions which provide improved benefits such as improved substantivity, reduced migration as well as improved sunscreen efficiency which have a surface tension of greater than about 30 dynes/cm, when measured on a 3.33% (w/w) aqueous solution of the emulsion, which possess a wax component having a required HLB between about 1 and about 8.

These and other objects will become readily apparent from the detailed description that follows.

SUMMARY OF THE INVENTION

The present invention relates to oil-in-water sunscreen emulsion compositions having improved efficiency for topical use and which provide an SPF of at least 8 comprising:
(a) from about 1% to about 20% of a sunscreen component consisting essentially of:
  i) from about 1% to about 100% of octocrylene;
  ii) from 0% to about 80% of ethylhexyl-p-methoxycinnamate; and
  iii) from 0% to about 80% of titanium dioxide;
(b) from about 0.025% to about 2.0% of a carboxylic copolymer comprising polymers of a monomeric mixture monomer selected from the group consisting of acrylic, methacrylic and ethacrylic acids, about 1 to about 3.5 weight percent of an acrylate ester of the formula:

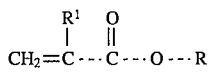

wherein R is hydrogen or an alkyl radical containing 10 to 30 carbon atoms and $R^1$ is hydrogen, methyl or ethyl, and 0.1 to 0.6 weight percent of a polymerizable cross-linking polyalkenyl polyether of a polyhydric alcohol containing more than one alkenyl ether group per molecule wherein the parent polyhydric alcohol contains at least 3 carbon atoms and at least 3 hydroxyl groups;
(c) from about 0.1% to about 5.0% of a film-forming copolymer;
(d) from about 0.1% to about 10% of a wax component having a required HLB of from about 1 to about 8 and a melting point greater than about 50° C.; and
(e) a safe and effective amount of a topical carrier;
wherein said sunscreen emulsion, when diluted as a 3.33% (w/w) aqueous solution, has a surface tension greater than about 30 dynes/cm, preferably greater than about 31 dynes/cm, and most preferably greater than about 32 dynes/cm.

The present invention further relates to a method of inhibiting the deleterious effects of ultraviolet light exposure to skin comprising applying a safe and photoprotectively effective amount of these compositions.

All percentages and ratios used herein are by weight of the total composition and all measurements made at 25° C., unless otherwise designated.

DETAILED DESCRIPTION OF THE INVENTION

In accordance with the present invention, moisture resistant skin treatment compositions, such as sunscreen and sun block formulations, and moisturizer formulations are provided, which compositions have improved efficiency and are in the form of a oil-in-water emulsion which contains water, emollients, emulsifiers, thickeners, preservatives, antioxidants and the like and one or more known ultraviolet absorbing compounds (in the case of sunscreen or sun block formulations).

Surface Tension

The surface tension of the emulsions of the present invention are determined experimentally as 1%–50% (w/w) aqueous solutions using a Kruss model no. K12 processor tensiometer (available from Kruss, W.Germany). The measurements are made at 25° C. using either the Wilhelmy plate method at a dipping distance of 1 mm or the Du Nouy ring method, with a return distance of 3.33% and a margin searching value of 1 mg. Preferably the surface tension measurements are determined as 3.33% (w/w) aqueous solutions using the Wilhelmy plate method.

Sunscreens.

The compositions of the present invention contain from about 1% to about 20% of a sunscreen component consisting essentially of:
  i) from about 1% to about 100% of octocrylene;
  ii) from 0% to about 80% of ethylhexyl-p-methoxycinnamate (available as Parsol MCX from Givaudan Corporation); and
  iii) from 0% to about 80% of titanium dioxide;

Preferably, the sunscreen component comprises from about 1% to about 10%, preferably from about 3% to about 7% octocrylene, from about 1% to about 80%, preferably from about 3% to about 7.5% of ethylhexyl-p-methoxycinnamate and from about 0.5% to about 80%, preferably from about 0.5% to about 3.0% titanium dioxide.

Octocrylene (2-ethylhexyl 2-cyano-3,3-diphenylacrylalte) is fully described in U.S. Pat. No. 3,215,724, to Stobel et al., issued Nov. 2, 1965; and BASF Provisional Technical Leaflet, "Uninul$^R$ Grades: UV Absorber for Cosmetic Products"; both of these references are incorporated herein by reference in their entirety.

This sunscreen component can be used alone or in combination with a wide variety of conventional sunscreening agents. Sagarim, et al., at Chapter VIII, pages 189 et seq., of *Cosmetics Science and Technology*, disclose numerous suitable agents. Specific suitable sunscreening agents include, for example: p-Aminobenzoic acid, its salts and its derivatives (ethyl, isobutyl, glyceryl esters; p-dimethylaminobenzoic acid); Anthranilates (i.e., o-aminobenzoates; methyl, octyl, amyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, -phenyl cinnamonitrile; butyl cinnamic pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol 3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzene, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyldibenzoylmethane; Butylmethoxydibenzoylmethane; 4-isopropyl-di-benzoylmethane; and camphor derivatives such as methyl benzylidene or benzylidene camphor; and mixtures thereof. Other sunscreens include zinc oxide, silica, iron oxide and the like. Without being limited by theory, it is believed that these inorganic materials provide a sunscreening benefit through reflecting, scattering, and absorbing harmful UV, visible, and infrared radiation.

A safe and photoprotectively effective amount of sunscreen may be used in the sunscreen compositions of the present invention. By "safe and photoprotectively" is meant an amount sufficient to provide photoprotection when the composition is applied, but not so much as to cause any side effects or skin reactions. Generally, the sunscreen agent may comprise from about 0.5% to about 20% of the composition. An additional sunscreen agent may comprise from about 0.5% to about 30%, preferably from about 0.5% to about 20%, of the composition. Exact amounts will vary depending upon the sunscreen chosen and the desired Sun Protection Factor (SPF).

SPF is a commonly used measure of photoprotection of a sunscreen against erythema. This number is derived from another parameter, the minimal erythemal dose (MED). MED is defined as the "lease exposure dose at a specified wavelength that will elicit a delayed erythem response". The MED indicates the amount of energy reaching the skin and the responsiveness of the skin to the radiation. The SPF of a particular photoprotector is obtained by dividing the MED of protected skin by the MED of unprotected skin. The higher the SPF, the more effective the agent in preventing sunburn. The SPF value tells how many times longer a person can stay in the sun with use of the sunscreen (compared to the same person with unprotected skin) before that person will experience 1 MED. For example, utilizing a sunscreen with an SPF of 6 will allow an individual to stay in the sun six times longer before receiving 1 MED. As the SPF value of a sunscreen increases, the less chance exists for development of tanning of the skin. Commercially available sunscreening products have SPF values ranging from 2 to 50. The compositions of the present invention preferably provide an SPF value of at least 8.

Also particularly useful along with the sunscreen component of the present invention are those sunscreens disclosed in U.S. Pat. No. 4,937,370, to Sabatelli, issued Jun. 26, 1990; and Sabatelli et al., U.S. patent application Ser. No. 054,046 (filed Jun. 2, 1987). The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N(2-ethylhexyl) methylaminobenzoic acid ester with 4-hydroxydibenzoylmethane; 4-N,N-(2-ethylhexyl)methylaminobenzoic acid ester of 2-hydroxy-4-(2-hydroxyethoxy) benzophenone; 4-N,N-(2-ethylhexyl) methylaminobenzoic acid ester of 4-(2-hydroxyethoxy)dibenzoylmethane; N-N-di-(2-ethylhexyl)-4-aminobenzoic acid ester of 2-hydroxy-4-(2-hydroxyethoxy)benzophenone, and N,N-di-(2-ethylhexyl) 4-aminobenzoic acid ester of 4-(2-hydroxyethoxy)dibenzoylmethane and mixtures thereof. Emulsifier.

The compositions of the present invention also essentially comprise at least one emulsifier comprising a carboxylic acid copolymer. These copolymers consist essentially of a colloidally water-soluble polymer of acrylic acid crosslinked with a polyalkenyl alkenyl polyether of a polyhydric alcohol, and optionally an acrylate ester or a polyfunctional vinylidene monomer.

Preferred carboxylic acid copolymers useful in the present invention are polymers of a monomeric mixture containing 95.9 to 98.8 weight percent of an olefinically unsaturated carboxylic monomer selected from the group consisting of acrylic, methacrylic and ethacrylic acids; about 1 to about 3.5 weight percent of an acrylate ester of the formula:

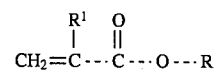

wherein R is an alkyl radical containing 10 to 30 carbon atoms and $R^1$ is hydrogen, methyl or ethyl; and 0.1 to 0.6 weight percent of a polymerizable cross-linking polyalkenyl polyether of a polyhydric alcohol containing more than one alkenyl ether group per molecule wherein the parent polyhydric alcohol contains at least 3 carbon atoms and at least 3 hydroxyl groups.

Preferably, these polymers contain from about 96 to about 97.9 weight percent of acrylic acid and from about 2.5 to about 3.5 weight percent of acrylic esters wherein the alkyl group contains 12 to 22 carbon atoms, and $R^1$ is methyl, most preferably the acrylate ester is stearyl methacrylate. Preferably, the amount of crosslinking polyalkenyl polyether monomer is from about 0.2 to 0.4 weight percent. The preferred crosslinking polyalkenyl polyether monomers are allyl pentaerythritol, trimethylolpropane diallylether or allyl sucrose. These polymers are fully described in U.S. Pat. No. 4,509,949, to Huang et al., issued Apr. 5, 1985, this patent being incorporated herein by reference.

Other preferred copolymers useful in the present invention are the polymers which contain at least two monomeric ingredients, one being a monomeric olefinically-unsaturated carboxylic acid, and the other being a polyalkenyl, polyether of a polyhydric alcohol. Additional monomeric materials may be present in the monomeric mixture if desired, even in predominant proportion.

The first monomeric ingredient useful in the production of these carboxylic polymers are the olefinically-unsaturated carboxylic acids containing at least one activated carbon-to-carbon olefinic double bond, and at least one carboxyl group. The preferred carboxylic monomers are the acrylic acids having the general structure

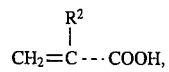

wherein $R^2$ is a substituent selected from the class consisting of hydrogen, halogen, and the cyanogen (—C≡N) groups, monovalent alkyl radicals, monovalent alkaryl radicals and monovalent cycloaliphatic radicals. Of this class, acrylic, methacrylic, and ethacrylic acid are most preferred. Another useful carboxylic monomer is maleic anhydride or the acid. The amount of acid used will be from about 95.5 to about 98.9 weight percent of the total monomers used. More preferably the range will be from about 96 to about 97.9 weight percent.

The second monomeric ingredient useful in the production of these carboxylic polymers are the polyalkenyl polyethers having more than one alkenyl ether grouping per molecule. The most useful possess alkenyl groups in which an olefinic double bond is present attached to a terminal methylene grouping, $CH_2=C<$.

The additional monomeric materials which may be present in the polymers include polyfunctional vinyl idene monomers containing at least two terminal $CH_2<$ groups, including for example, butadiene, isoprene, divinyl benzene, divinyl naphthalene, allyl acrylates, and the like. These polymers are fully described in U.S. Pat. No. 2,798,053, to Brown, H. P., issued Jul. 2, 1957, this patent being incorporated herein by reference.

Examples of carboxylic acid copolymers useful in the present invention include Carbomer 934, Carbomer 941, Carbomer 950, Carbomer 951, Carbomer 954, Carbomer 980, Carbomer 981, Carbomer 1342, and Acrylates/$C_{10-30}$ Alkyl Acrylate Cross Polymers (available as Carbopol 934, Carbopol 941, Carbopoly 950, Carbopol 951, Carbopol 954, Carbopol 980, Carbopol 981, Carbopol 1342, and the Pemulen series, respectively, from B.F. Goodrich).

Other carboxylic acid copolymers useful in the present invention include sodium salts of acrylic acid/acrylamide copolymers sold by the Hoechst Celanese Corporation under the trademark of Hostaceren PN73. Also included are the hydrogel polymers sold by lipo Chemicals Inc. under the trademark of HYPAN hydrogels. These hydrogels consist of crystalline plicks of nitrites on a C—C backbone with various other pendant groups such as carboxyls, amides, and amidines. An example would include HYPAN SA100H, a polymer powder available from Lipo Chemical.

Neutralizing agents suitable for use in neutralizing acidic group containing copolymers herein include sodium hydroxide, potassium hydroxide, ammonium hydroxide, monoethanolamine, diethanolamine, triethanolamine, tetrahydroxypropyl ethylenediame (available as the Quadrol$^R$ series from BASF), tris, arginine, triisopropylamine and lysine.

The carboxylic acid copolymers can be used individually or as a mixture of two or more polymers and comprise from about 0.025 to about 0.75, preferably from about 0.05 to about 0.25 and most preferably from about 0.075 to about 0.175 percent of the compositions of the present invention.

Wax Component.

An essential component of the compositions herein is a non-polar wax component having a required HLB of from about 1 to about 8, more preferably from about 1 to about 7 and a melting point greater than about 50° C., and preferably greater than about 60° C.

Useful waxes include ester waxes, diester waxes, hydrocarbon waxes, silicone waxes and triglyceride waxes and mixtures thereof.

It is important that the HLB measurements be determined experimentally rather than from empirical calculations. The HLB (short for "Hydrophile-Lipophile Balance") value system is fully described, and values for various materials are provided, in the publication *The HLB System, A Time-Saving Guide to Emulsifier Selection* (published by ICI Americas Inc., Wilmington, Delaware; 1984), the disclosures of which are incorporated herein by reference in their entirety.

Useful ester waxes include $C_{16}$–$C_{40}$ alcohols esterlied with $C_{16}$–$C_{40}$ fatty acid, diesters of $C_{16}$–$C_{40}$ fatty acid where the alcohol is propylene glycol, ethylene glycol, polyethylene glycol, polypropylene glycol, $C_{12}$–$C_{40}$, triglycerides or $C_{18}$–$C_{40}$ diglycerides, pentaerythitol tri- or tetra- esters of $C_{12}$–$C_{40}$ fatty acids, $C_{18}$–$C_{40}$ fatty acids of sorbitan triesters. Useful synthetic waxes include FischerTropsche waxes. Useful hydrocarbon waxes include paraffin, microcrystalline waxes, and mixtures thereof. Useful diester waxes include Syncrowax ERL-C (available from Croda); $C_{18}$–$C_{40}$ fatty acid diester and propylene glycol diester waxes including propylene glycol distearate and glycol distearate. Useful triglyceride waxes include Syncrowax HGL-C, Syncrowax HRC, Syncrowax HRS-C (all available from Croda Inc.), tristearin, trimyristate, castor wax and fully hydrogenated vegetable or animal oils as well as alkyloxysilicone waxes (such as Dow Corning 580 Wax) and mixtures thereof.

Those waxes those useful in the compositions of this invention are disclosed in the following, all of which are incorporated by reference herein in their entirety: U.S. Pat. No. 4,049,792, to Elsnau, issued Sept. 20, 1977; U.S. Pat. No. 4,151,272, to Geary et al., issued Apr. 24, 1975; U.S. Pat. No. 4,229,432, to Geria, issued Oct. 21, 1980; U.S. Pat. No. 4,280,994, to Turney, issued Jul. 28, 1981; U.S. Pat. No. 4,126,679, to Davy et al., issued Nov. 21, 1978; and European Patent Application Publication Number 117,070, to May, published Aug. 29, 1984, "The Chemistry and Technology of Waxes", A. H. Warth, 2nd Edition, reprinted in 1960, Reinhold Publishing Corporation, pp 391–393 and 421; "The Petroleum Chemicals Industry", R. F. Goldstein and A. L. Waddeam, 3rd Edition (1967), E. & F. N. Span Ltd., pp 33–40; "The Chemistry and Manufacture of Cosmetics", M. G. DeNavarre, 2nd edition (1970), Van Nostrand & Company, pp 354–376; and in "Encyclopedia of Chemical Technology":, Vol. 24, Kirk-Othmer, 3rd Edition (1979) pp 466–481.

Film-forming Copolymer

The compositions of the present invention also essentially comprise a film-forming copolymer at a level of from about 0.1% to about 5.0%, preferably from about 0.1% to about 2%.

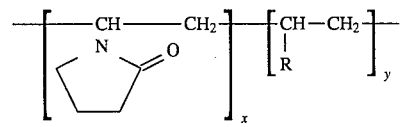

where R is a $C_{12}$–$C_{30}$ straight chain alkyl and preferably a $C_{18}$–$C_{22}$ straight chain alkyl and wherein the ratio of x to y is from about 1:5 to about 5:1. A particularly preferred copolymer is 1-eicosene polymer with 1-ethenyl-2-pyrrolidinone available from GAF Chemical Corporation as Ganex V-220$^R$.

Solubility Parameters of Oil Phase Components

The "oil phase components" of the compositions of the instant invention are those ingredients which are generally non-polar and have limited solubility in water.

The oil phase components of the present invention are herein defined to include the sunscreens (such as ethylhexyl-p-methoxycinnamte), waxes (such as stearoxy trimethylsilane/searyl alcohol, and tristearin), esters (such as isoarchidyl neopentanoate), substantivity and film-forming copolymers (such as polyvinylpyrollidone/eicosene copolymer), hydrocarbons, and other suitable materials.

The solubility parameter of a material, is defined as the square root of the cohesive energy density for that material. Knowing the chemical structure of a material, the solubility parameter is readily calculated from the additive group contributions for heat of vaporization and molar volume as shown by equation (1).

$$\delta = \left( \frac{\sum_i E_i}{\sum_i m_i} \right)^{1/2} \qquad \text{equation (1)}$$

wherein $\Sigma E_i$=the sum of the heat of vaporization additive group contributions $\Sigma m_i$=the sum of the molar volume additive group contributions The additive group contributions for heat of vaporztion and molar volume used to calculate the solubility parameters of the present invention are tabulated in Barton, A.F.M. *Handbook of Solubility Parameters*, CRC Press, Chapter 6, Table 3, pp. 64–66 (1985). The relationship of equation (1) is described in Fedors, R. F., "A Method for Estimating Both the Solubility Parameters and Molar Volumes of Liquids", *Polymer Engineering and Science*, vol. 14, no. 2, pp. 147–154 (February 1974), these two publications being incoporated herein by reference.

Calculated solubility parameters obey the law of mixtures such that the calculated solubility parameter for a mixture of materials is given by the weighted average of the calculated solubility parameters for each component of that mixture. See, *Handbook of Chemistry and Physics*, 57th edition, CRC Press, p. C-726 (1976–1977), this publication being incorporated herein by reference.

All calculated solubility parameters of the present invention are reported in units of $(cal/cm^3)^{1/2}$. The tabulated values for the additive group contributions for heat of vaporization in the *Handbook of Solubility Parameters* are reported in units of kJ/mol. These values are converted to cal/mol using the relationships:

1 J/mol=0.239006 cal/mol and 100 J=1 kJ. See Gordon, A. J. et al., *The Chemist's Companion*, John Wiley & Sons, pp. 456–463, (1972), this publication being incorporated herein by reference.

Optional Components
Emollients.

The compositions of the present invention preferably comprise at least one emollient. Useful emollients have a required HLB below about 10. Preferred emollients are volatile silicone oils, non-volatile emollients, and the highly branched hydrocarbons known as the Permethyl 99 through 108A series (available from Permethyl Corporation) and mixtures thereof. The compositions of the present invention more preferably comprise at least one volatile silicone oil which functions as a liquid emollient, or especially in a mixture of volatile silicone oils and non-volatile emollients The term "volatile" as used herein, refers to those materials which have a measurable vapor pressure at ambient temperature.

Volatile silicone oils useful in the compositions of the present invention are preferably cyclic. The following formula illustrates cyclic volatile polydimethylsiloxanes useful in the compositions disclosed herein:

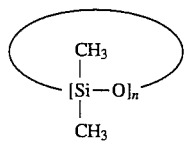

wherein n equals about 3 to about 7. Linear polydimethylsiloxanes contain from about 3 to about 9 silicon atoms per molecule and have the following general formula:

wherein n equals about 1 to about 7. Linear volatile silicone materials generally have viscosities of less than about 5 centistokes at 25° C. while cyclic materials typically have viscosities of less than about 10 centistokes. A description of various volatile silicone oils is found in Todd, et al., "Volatile Silicone Fluids for Cosmetics", *Cosmetics & Toiletries*, 91, pages 27–32 (1976), the disclosures of which are incorporated by reference herein in their entirety.

Examples of preferred volatile silicone oils useful herein include: Dow Corning 344, Dow Corning 345, and Dow Corning 200 (manufactured by Dow Corning Corp.); Silicone 7207 and Silicone 7158 (manufactured by the Union Carbide Corp.); SF 1202 (manufactured by General Electric); and SWS-03314 (manufactured by SWS Silicones, Inc.).

The present compositions also preferably contain one or more non-volatile emollients. Such materials include fatty acid and fatty alcohol esters, hydrocarbons, non-volatile silicone oils, and mixtures thereof. Emollients among those useful herein are described in 1 *Cosmetics, Science and Technology* 27–104 (M. Balsam and E. Sagarin, Ed.; 1972), and U.S. Pat. No. 4,202,879, to Shelton, issued May 13, 1980 (both incorporated by reference herein).

Non-volatile silicone oils useful as an emollient material include polyalkylsiloxanes and polyalklyarylsiloxanes. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 100 centistokes at 25° C. Such polyalkyl siloxanes include the Vicasil series (sold by General Electric Company) and the Dow Corning 200 series (sold by Dow Corning Corporation). Polyalkylaryl siloxanes include poly methylphenyl siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation).

Non-polar fatty acid and fatty alcohol esters useful herein as an emollient material include, for example, ethyl hexyl palmitate, isodecyl neopentanoate, octadodecyl benzoate, diethyl hexyl maleate and PPG-2 myristyl ether propionate. Hydrocarbons such as isohexadecane (e.g., Permethyl 101A supplied by Presperse), petrolatum and USP light (e.g. Klearol$^R$) or heavy (e.g. Kaydol$^R$) mineral oils are also useful as emollients.

The emollients typically comprise in total from about 1% to about 50%, preferably from about 1% to about 25%, and more preferably from about 1% to about 10% by weight of the compositions of the present invention.

Optional Oil Soluble and Water Soluble Components

The compositions of the present invention may also contain in addition to the aforementioned components, a wide variety of additional oil soluble materials and/or water soluble materials.

These other oil soluble materials include esters such as cetearyl palmitate, lauryl myristate and isopropyl palmitate; oils such as castor oil, jojoba oil, cottonseed oil, peanut oil and sesame oil; waxes such as petrol atum, ceresin wax, carnauba wax, beeswax, and castor wax; cetyl palmitate; oil dispersable powders such as aluminum starch octenyl succinate. Sterols such as soya sterol, cholesterol and phytosterol are also useful herein. Highly preferred for use herein are isodecyl neopentanoate, isoarachidyl neopentanoate, and isohexadecane and mixtures thereof.

These optional oil phase materials may individually comprise up to about 20% by weight of the total sunscreen composition, preferably from about 10% to about 15%.

Additional water soluble materials may also be present in the compositions of this invention. Included are humectants such as glycerine, hexylene glycol, sorbitol, propylene glycol, alkoxylated glucose and hexanetriol; thickening agents; hydroxyethyl cellulose, carboxymethyl cellulose, vegetable gums and clays such as Veegum$^R$ (magnesium aluminum silicate, R. T. Vanderbilt, Inc.); proteins and polypeptides; ethanolamine, sodium hydroxide, potassium hydroxide or citric acid; and chleators such as disodium EDTA, if desired.

Other water-soluble materials include urea; guanidine; glycolic acid and glycolate salts (e.g. ammonium and quaternary alkyl ammonium); lactic acid and lactate salts (e.g. ammonium and quaternary alkyl ammonium); polyhydroxy alcohols such as sorbitol, glycerin, hexanetriol, propylene glycol, hexylene glycol and the like; polyethylene glycol; sugars and starches; sugar and starch derivatives (e.g. alkoxylated glucose); panthenol; hyaluronic acid; lactamide monoethanol amine; acetami de monoethanol amine; and mixtures thereof.

Without being limited by theory, it is recognized that relatively high levels, i.e. greater than 2%, of these water-soluble components may negatively impact the SPF of the final formulation. Therefore, it is preferable to limit the levels of these ingredients to no greater than 2% of the formulations of the instant invention.

Additional Ingredients

A variety of additional ingredients may be added to the emulsion compositions of the present invention. These additional ingredients include various polymers for aiding the film-forming properties and substantivity of the formulations, preservatives for maintaining the antimicrobial integrity of the compositions, antioxidants, and agents suitable for aesthetic purposes such as fragrances, pigments, and colorings. Various vitamins can also be included in the compositions of the present invention. Non-limiting examples include Vitamin A, and derivatives thereof, ascorbic acid, Vitamin B complexes and derivatives thereof such as panthothenic acid, biotin, Vitamin D, Vitamin E and derivatives thereof such as tocopheryl acetate, and mixtures thereof can also be used.

The pH of the sunscreen compositions herein is preferably in the range of from about 4.5 to about 9.

For an aqueous emulsion sunscreen composition of the present invention, the mean particle size of the dispersed oil phase materials (e.g., sunscreen agent, polymer, perfumes, etc.) dispersed in the aqueous phase may be in the range of from about 2 to about 10 microns with greater than about 75% of the particles being less than about 12 microns.

Also useful in levels that total less than about 0.5% are surfactants such as TEA stearate salts, alkali neutralized mono- and dialkyl phosphates including diethanolamine mono- and di- cetyl phosphate (available from Givaudan as Amphisol) and hydroxy cetyl phosphate (available from Henkel as Forlanit E). Of course, the emulsion must maintain a surface tension greater than about 30 dynes/cm as measured on a 3.33% by weight aqueous solution of the emulsion.

The pharmaceutically-acceptable sunscreen carriers, in total, typically comprise from about 0.1% to about 99.8% by weight of the sunscreen compositions of the present invention, preferably from about 80% to about 99%, and most preferably from about 85% to about 95%.

The compositions of the present invention may be prepared using the method described in the examples hereinafter.

The following non-limiting examples illustrate embodiments of the subject invention wherein both essential and optional ingredients are combined. It is to be understood that these examples are for illustrative purposes only and are not to be construed as limiting the scope of the invention thereto.

EXAMPLE

| Ingredients | % Weight |
| --- | --- |
| Phase A | |
| Water | QS100 |
| Carbomer 954[1] | 0.24 |
| Carbomer 1342[2] | 0.16 |
| Disodium EDTA | 0.05 |
| Phase B | |
| Isoarachidyl Neopentanoate[3] | 2.00 |
| PVP Eicosene Copolymer[4] | 2.00 |
| Octocrylene | 7.00 |
| Octyl Methoxycinnamate | 3.00 |
| Titanium Dioxide | 1.00 |
| Cetyl Palmitate | 0.75 |
| Stearoxytrimethylsilane (and) Stearyl Alchohol[5] | 0.50 |
| Glyceryl Tribehenate[6] | 0.75 |
| Dimethicone | 1.00 |
| Tocopheryl Acetate | 0.10 |
| DEA-Cetyl Phosphate | 0.20 |
| Phase C | |
| Water | 2.00 |
| Triethanolamine 99% | 0.60 |
| Phase D | |
| Water | 2.00 |
| Butylene Glycol | 1.00 |
| DMDM Hydantoin (and) Iodopropynyl Butylcarbamate | 0.25 |
| dL Panthenol | 1.00 |
| Phase E | |
| Cyclomethicone | 1.00 |

[1]Available as Carbopol ® 954 from B. F. Goodrich.
[2]Available as Carbopol ® 1342 from B. F. Goodrich.
[3]Available as Elefac I-205 from Bernel Chemical.
[4]Available as Ganex V-220 from GAF Corporation.
[5]Available as DC 580 Wax from Dow Corning.
[6]Available as Synchrowax HRC from Croda.
[7]Available as Glydant Plus from Lonza.

In a suitable vessel the Phase A ingredients are dispersed in the water and heated to 75°–85° C. In a separate vessel the Phase B ingredients (except DEA-Cetyl Phosphate) are combined and heated to 85°–90° C. until melted. Next, the DEA-Cetyl Phosphate is added to the liquid Phase B and stirred until dissolved. This mixture is then added to Phase A to form the emulsion. The Phase C ingredients are combined until dissolved and then added to the emulsion. The emulsion is then cooled to 40°–45° C. with continued mixing. In another vessel, the Phase D ingredients are heated with mixing to 40°–45° C. until a clear solution is formed and this solution is then added to the emulsion. Finally, the emulsion is cooled to 35° C. and the Phase E ingredient is added and mixed.

This emulsion is useful for topical application to the skin to provide protection from the harmful effects of ultraviolet radiation.

EXAMPLE II

| Ingredients | % Weight |
| --- | --- |
| Phase A | |
| Water | QS100 |
| Carbomer 954 | 0.14 |
| Acrylates/C$_{10}$-30 Alkyl Acrylate Crosspolymer[1] | 0.16 |
| Disodium EDTA | 0.05 |
| Phase B | |
| Isohexedecane[2] | 2.00 |
| PVP Eicosene Copolymer | 2.00 |
| Octocrylene | 7.00 |
| Octyl Methoxycinnamate | 3.00 |
| Titanium Dioxide | 3.00 |
| Cetyl Palmitate | 0.75 |
| Stearoxytrimethylsilane (and) Stearyl Alchohol | 0.50 |
| Glyceryl Tribehenate | 0.75 |
| Dimethicone | 1.00 |

-continued

| Ingredients | % Weight |
|---|---|
| Tocopheryl Acetate | 0.10 |
| DEA-Cetyl Phosphate | 0.20 |
| Phase C | |
| Water | 2.00 |
| Triethanolamine 99% | 0.40 |
| Phase D | |
| Water | 2.00 |
| Butylene Glycol | 1.00 |
| DMDM Hydantoin (and) Iodopropynyl Butylcarbamate | 0.25 |
| dL Panthenol | 1.00 |
| Phase E | |
| Cyclomethicone | 1.00 |

[1] Available as Pemulan TR-1 from B. F. Goodrich
[2] Available as Permethyl 101A from Presperse (South Plainfield, New Jersey)

An emulsion is prepared from the above ingredients employing the method described in Example A.

EXAMPLE III

| Phase A | |
|---|---|
| Water | QS100 |
| Carbomer 954 | 0.24 |
| Carbomer 1342 | 0.16 |
| Disodium EDTA | 0.05 |
| Phase B | |
| Isoarachidyl Neopentanoate | 2.00 |
| PVP Eicosene Copolymer | 2.00 |
| Octocrylene | 7.00 |
| Cetyl Palmitate | 0.75 |
| Stearoxytrimethylsilane (and) Stearyl Alcohol | 0.50 |
| Glyceryl Tribehenate | 0.75 |
| Dimethicone | 1.00 |
| Tocopheryl Acetate | 0.10 |
| DEA-Cetyl Phosphate | 0.20 |
| Phase C | |
| Water | 2.00 |
| Triethanolamine 99% | 0.60 |
| Phase D | |
| Water | 2.00 |
| Butylene Glycol | 2.00 |
| DMDM Hydantoin (and) Iodopropynyl Butylcarbamate | 0.25 |
| dL Panthenol | 1.00 |
| Phase E | |
| Cyclomethicone | 1.00 |

An emulsion is prepared from the above ingredients employing the method described in Example A.

This emulsion is useful for topical application to the skin to provide protection from the harmful effects of ultraviolet radiation.

EXAMPLE IV

| Phase A | |
|---|---|
| Water | QS100 |
| Carbomer 954 | 0.24 |
| Carbomer 1342 | 0.16 |
| Disodium EDTA | 0.05 |
| Phase B | |
| Isoarachidyl Neopentanoate | 2.00 |
| PVP Eicosene Copolymer | 2.00 |
| Octocrylene | 7.00 |
| Titanium Dioxide | 1.00 |
| Cetyl Palmitate | 0.75 |
| Stearoxytrimethylsilane (and) Stearyl Alcohol | 0.50 |
| Glyceryl Tribehenate | 0.75 |
| Dimethicone | 1.00 |
| Tocopheryl Acetate | 0.10 |
| DEA-Cetyl Phosphate | 0.20 |
| Phase C | |
| Water | 2.00 |
| Triethanolamine 99% | 0.60 |
| Phase D | |
| Water | 2.00 |
| Butylene Glycol | 2.00 |
| DMDM Hydantoin (and) Iodopropynyl Butylcarbamate | 0.25 |
| dL Panthenol | 1.00 |
| Phase E | |
| Cyclomethicone | 1.00 |

An emulsion is prepared from the above ingredients employing the method described in Example A.

This emulsion is useful for topical application to the skin to provide protection from the harmful effects of ultraviolet radiation.

EXAMPLE V

| Phase A | |
|---|---|
| Water | QS100 |
| Carbomer 954 | 0.24 |
| Carbomer 1342 | 0.16 |
| Disodium EDTA | 0.05 |
| Phase B | |
| Isoarachidyl Neopentanoate | 2.00 |
| PVP Eicosene Copolymer | 2.00 |
| Octyl Methoxycinnamate | 3.00 |
| Octocrylene | 7.00 |
| Cetyl Palmitate | 0.75 |
| Stearoxytrimethylsilane (and) Stearyl Alcohol | 0.50 |
| Glyceryl Tribehenate | 0.75 |
| Dimethicone | 1.00 |
| Tocopheryl Acetate CG | 0.10 |
| DEA-Cetyl Phosphate | 0.20 |
| Phase C | |
| Water | 2.00 |
| Triethanolamine 99% | 0.60 |
| Phase D | |
| Water | 2.00 |
| Butylene Glycol | 2.00 |
| DMDM Hydantoin (and) Iodopropynyl Butylcarbamate | 0.25 |
| dL Panthenol | 1.00 |
| Phase E | |
| Cyclomethicone | 1.00 |

An emulsion is prepared from the above ingredients employing the method described in Example A.

This emulsion is useful for topical application to the skin to provide protection from the harmful effects of ultraviolet radiation.

What is claimed is:

1. An oil-in-water sunscreen emulsion composition having improved efficiency for topical use and which provides an SPF of at least 8 comprising:
   (a) from about 1% to about 20% of a sunscreen component consisting essentially of:
      i) from about 1% to about 100% of octocrylene;
      ii) from 0% to about 80% of ethylhexyl-p-methoxy cinnamate; and
      iii) from 0% to about 80% titanium dioxide;
   (b) from about 0.025% to about 2.0% of a carboxylic copolymer comprising polymers of a monomeric mixture selected from the group consisting of acrylic, methacrylic and ethacrylic acids, about 1 to about 3.5 weight percent of an acryl ate ester of the formula:

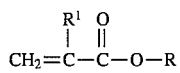

wherein R is hydrogen or an alkyl radical containing 10 to 30 carbon atoms and $R^1$ is hydrogen, methyl or ethyl, and 0.1 to 0.6 weight percent of a polymerizable cross-linking polyalkenyl polyether of a polyhydric alcohol containing more than one alkenyl ether group per molecule wherein the parent polyhydric alcohol contains at least 3 carbon atoms and at least 3 hydroxyl groups;
   (c) from about 0.1% to about 5.0% of a film-forming copolymer of the formula:

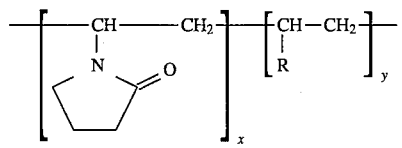

where R is a $C_{12}$–$C_{30}$ straight alkyl chain and wherein the ratio of x to y is from about 1:5 to 5:1;
   (d) from about 0.1% to about 10% of a wax component having a required HLB of from about 1 to about 8 and a melting point greater than about 50° C. wherein said wax component is selected from the group consisting of ester waxes, hydrocarbon waxes, diester waxes, silicone waxes, triglyceride waxes, and mixtures thereof; and
   (e) a safe and effective amount of a pharmaceutically-acceptable sunscreen carrier;
wherein said sunscreen emulsion, when diluted as a 3.33% (w/w) aqueous solution, has a surface tension greater than about 30 dynes/cm.

2. A sunscreen composition according to claim 1 wherein the sunscreen component comprises from about 1% to about 10% of octocrylene, from about 3% to about 7.5% of ethylhexyl-p-methoxycinnamate and from about 0.5% to about 3.0% of titanium dioxide.

3. A sunscreen composition according to claim 2 wherein said wax component has a melting point greater than about 60° C.

4. A sunscreen composition according to claim 3 wherein said ester wax is selected from the group consisting of $C_{16}$–$C_{40}$ alcohols esterified with $C_{16}$–$C_{40}$ fatty acids, diesters of $C_{16}$–$C_{40}$ fatty acids where the alcohol is propylene glycol, diesters of $C_{16}$–$C_{40}$ fatty acids where the alcohol is ethylene glycol, diesters of $C_{16}$–$C_{40}$ fatty acids where the alcohol is polyethylene glycol, diesters of $C_{16}$–$C_{40}$ fatty acids where the alcohol is polypropylene glycol, $C_{12}$–$C_{40}$ triglycerides $C_{18}$–$C_{40}$ diglycerides, pentaerythritol tri-esters of $C_{12}$–$C_{40}$ fatty acids, pentaerythritol tetra-esters of $C_{12}$–$C_{40}$ fatty acids, $C_{18}$–$C_{40}$ fatty acids of sorbitan triesters, and mixtures thereof.

5. A sunscreen composition according to claim 4 wherein said wax component has a required HLB of from about 1 to about 7.

6. A sunscreen composition according to claim 5 wherein said triglyceride wax is selected from the group consisting of $C_{18}$–$C_{36}$ acid triglyceride, tribehenin, tribehenin (and) calcium behenate, tristearin, trimyristate, castor wax, hydrogenated vegetable oil, alkyloxysilicone waxes, and mixtures thereof.

7. A sunscreen composition according to claim 6 wherein said filmforming copolymer is 1-eicosene polymer with 1-ethenyl-2-pyrrolidinone.

8. A method for protecting the skin of humans or lower animals from the effects of ultraviolet radiation, said method comprising topically applying to the skin of the human or lower animal an effective coating of a sunscreen composition according to claim 1.

9. A method for protecting the skin of humans or lower animals from the effects of ultraviolet radiation, said method comprising topically applying to the skin of the human or lower animal an effective coating of a sunscreen composition according to claim 2.

10. A method for protecting the skin of humans or lower animals from the effects of ultraviolet radiation, said method comprising topically applying to the skin of the human or lower animal an effective coating of a sunscreen composition according to claim 3.

11. A method for protecting the skin of humans or lower animals from the effects of ultraviolet radiation, said method comprising topically applying to the skin of the human or lower animal an effective coating of a sunscreen composition according to claim 4.

12. A method for protecting the skin of humans or lower animals from the effects of ultraviolet radiation, said method comprising topically applying to the skin of the human or lower animal an effective coating of a sunscreen composition according to claim 5.

13. A method for protecting the skin of humans or lower animals from the effects of ultraviolet radiation, said method comprising topically applying to the skin of the human or lower animal an effective coating of a sunscreen composition according to claim 6.

* * * * *

UNITED STATES PATENT AND TRADEMARK OFFICE
CERTIFICATE OF CORRECTION

PATENT NO. : 5,547,659

DATED : August 20, 1996

INVENTOR(S) : Marie Antoinette Rinaldi, Larry Richard Robinson

It is certified that error appears in the above-identified patent and that said Letters Patent is hereby corrected as shown below:

At Column 1, line 51 "*Science*, 3," should read --*Science*, 4,--.

At Column 2, line 27 "water in-oil" should read --water-in-oil--.

At Column 4, line 33 "cinnamic" should read --cinnamoyl--.

At Column 5, line 12 "erythem" should read --erythema--.

At Column 5, line 59 "polyalkenyl alkenyl polyether" should read --polyalkenyl polyether--.

At Column 6, line 58 "vinyl idene" should read --vinylidene--.

At Column 7, line 14 "SA 100H" should read --SA100 H--.

At Column 7, line 44 "esterlied" should read --esterfied--.

At Column 8, line 17 the phrase --A preferred film-forming copolymer is of the formula:-- should be inserted before the formula diagram.

At Column 8, line 52 " $\Sigma E_i$ " should read -- $\sum_i E_i$ --.

At Column 8, line 54 " $\Sigma m_i$ " should read -- $\sum_i m_i$ --.

At Column 9, line 11 "100 J=1 kJ" should read --1000 J=1 kJ--.

At Column 10, line 10 "about 100 centistokes" should read --about 1000 centistokes--.

At Column 10, line 39 "petrol atum" should read --petrolatum--.

At Column 10, line 66 "monoethanol amine" should read --monoethanolamine--.

At Column 10, line 66 "acetami de monoethanol amine" should read --acetamide monoethanolamine--.

At Column 11, line 53 "EXAMPLE" should read --EXAMPLE I--.

At Column 15, line 17 "acryl ate" should read --acrylate--.

UNITED STATES PATENT AND TRADEMARK OFFICE
CERTIFICATE OF CORRECTION

PATENT NO. :   5,547,659

DATED      :   August 20, 1996

INVENTOR(S) :   Marie Antoinette Rinaldi, Larry Richard Robinson

It is certified that error appears in the above-identified patent and that said Letters Patent is hereby corrected as shown below:

At Column 16, line 9 "tri-esters" should read --triesters--.

Signed and Sealed this

Twenty-first Day of January, 1997

Attest:

BRUCE LEHMAN

*Attesting Officer*      *Commissioner of Patents and Trademarks*